United States Patent [19]
Höss et al.

[11] Patent Number: 5,804,371
[45] Date of Patent: Sep. 8, 1998

[54] HAPTEN-LABELLED PEPTIDES

[75] Inventors: Eva Höss, Starnberg; Christoph Seidel, Weilheim; Ursula-Henrike Wienhues, Krailling; Elke Faatz, Pähl; Urban Schmitt, Oberhausen, all of Germany

[73] Assignee: Boehringer Mannheim GmbH, Mannheim, Germany

[21] Appl. No.: 615,279

[22] PCT Filed: Jul. 24, 1995

[86] PCT No.: PCT/EP95/02921

§ 371 Date: Jun. 13, 1996

§ 102(e) Date: Jun. 13, 1996

[87] PCT Pub. No.: WO96/03423

PCT Pub. Date: Feb. 8, 1996

[30] Foreign Application Priority Data

Jul. 25, 1994 [DE] Germany .......................... 44 26 276.0
Aug. 31, 1994 [DE] Germany .......................... 44 30 973.2

[51] Int. Cl.⁶ .......................... C12Q 1/70; G01N 33/576; G01N 33/569
[52] U.S. Cl. .............................. 435/5; 435/7.92; 435/974; 436/518; 436/820; 530/324; 530/325; 530/326; 530/820
[58] Field of Search .................................. 94/105; 435/5, 435/7.1, 7.9, 7.92, 974; 436/501, 518, 536, 543, 820; 530/300, 324, 325, 326, 327, 333, 334, 402, 807

[56] References Cited

U.S. PATENT DOCUMENTS 5,087,561  2/1992  Rosenblatt et al. ..................... 435/7.21

FOREIGN PATENT DOCUMENTS 0 218 347   4/1987  European Pat. Off. .
471407      2/1992  European Pat. Off. .
0 117 648   9/1994  European Pat. Off. .
44 02 756 A1 8/1995  Germany .
93/18054    9/1993  WIPO .

OTHER PUBLICATIONS

Kessler, "The digoxigenin:anti–digoxigenin (DIG) technology—a survey on the concept and realization of a novel bioanalytical indicator system", Mol. Cell. Probes 5, 161–205 (1991).
Patek, "Multistep deprotection for peptide chemistry", Int. J. Peptide Protein Res. 42, 97–117 (1993).
Bodanszky, "In search of new methods in peptide synthesis", Int. J. Peptide Protein Res. 25, 449–474 (1985).
Didziapetris et al., Penicillin acylase–catalyzed protection and deprotection of amino groups as a promising approach in enzymatic peptide synthesis, FEBS Letters 287(1–2):31–33, 1991.
Waldmann et al., New Enzymatic Protecting Group Techniques for the Construction of Peptides and Glycopeptides. Biomed. Biochim. Acta 50(10/11):S243–S248, 1991.
Chang et al., Expression in *Escherichia coli* of Open Reading Frame Gene Segments of HTLV–III, Science 228:93–96, 1985.

*Primary Examiner*—Michael P. Woodward
*Assistant Examiner*—Donna C. Wortman
*Attorney, Agent, or Firm*—Nakido Marmelstein Murray & Oram LLP

[57] ABSTRACT

The invention concerns a process for the production of hapten-labelled peptides which is characterized in that (a) a peptide with the desired amino acid sequence is synthesized on a solid phase from amino acid derivatives whose reactive side groups are blocked by protecting groups wherein the protecting groups on primary amino side groups are selected in such a way that, if desired, they can be selectively cleaved off, (b) protecting groups are cleaved to form at least one free primary amino group, (c) a hapten-active ester derivative is coupled to the at least one free primary amino group of the peptide and (d) if desired protecting groups that still remain are cleaved off, the hapten being selected from the group comprising sterols, bile acids, sexual hormones, corticoids, cardenolides, cardenolide-glycosides, bufadienolides, steroid-sapogenines and steroid alkaloids.

31 Claims, No Drawings

HAPTEN-LABELLED PEPTIDES

DESCRIPTION

The present invention concerns a process for the production of hapten-labelled peptides, hapten-labelled peptides obtainable by this process and the use of these peptides in an immunological method of detection.

The detection of immunoglobulins in body fluids, in particular in human sera, is used to diagnose infections with microorganisms, in particular viruses, such as HIV, hepatitis viruses etc. The presence of specific immunoglobulins in the examined sample is usually detected by reaction with one or several antigens that react with the specific immunoglobulins. Methods for the determination of specific immunoglobulins in the sample liquid must be sensitive, reliable, simple and rapid.

In recent years more and more detection systems based on non-radioactive marker groups have been developed in which the presence of an analyte, e.g. a specific antibody, in the examined sample can be determined with the aid of optical (e.g. luminescent or fluorescent), NMR-active or metal-precipitating detection systems.

EP-A-0 307 149 discloses an immunological test for an antibody in which two recombinant polypeptides are used as antigens one of which is immobilized on a solid phase and the other carries a marker group and both recombinant antigens are expressed in different organisms to increase the specificity of the test.

EP-A-0 366 673 discloses a method for the detection of antibodies in a sample in which an antibody is detected by reaction with a purified labelled antigen and with the same purified antigen in a solid phase-bound form. Human IgG is for example disclosed as an antigen.

EP-A-0 386 713 describes a method for the detection of antibodies against HIV using two solid supports in which various HIV antigens are immobilized on the two solid supports each of which is brought into contact with an aliquot of a sample and with a labelled HIV antigen wherein the presence of antibodies is detected by a positive reaction in at least one of the tests. Recombinantly produced polypeptides are disclosed as HIV antigens.

EP-A-0 507 586 describes a method for carrying out an immunological test for a specific immunoglobulin in which a sample is brought into contact with two antigens capable of binding the immunoglobulin, wherein the first antigen carries a group suitable for binding to a solid support and the second antigen carries a marker group. The marker group can be a direct marker group e.g. an enzyme, a chromogen, a metal particle, or also an indirect marker group i.e. the marker group attached to the antigen can react with a receptor for the marker group which in turn carries a signal-generating group. A fluorescein derivative is mentioned as an example of such an indirect marker group, the receptor of which is an antibody which in turn is coupled to an enzyme. Polypeptides such as the hepatitis B surface antigen are disclosed as antigens. SH groups are introduced into this antigen by derivatization which are used to couple the fluorescein.

EP-A-0 507 587 discloses a specific method for the detection of IgM antibodies in which the sample is incubated with a labelled antigen which is directed against the antibody to be detected and with a second antibody which is also directed against the antibody to be detected and is capable of binding to a solid phase.

In the immunological methods for detecting antibodies known from the state of the art polypeptide antigens are usually used which are normally produced by recombinant DNA methods. However, problems may occur when using such polypeptide antigens. Thus recombinant polypeptides can often only be produced in the form of fusion polypeptides in which case the fused part can lead to false positive results in the test. In addition polypeptides produced by recombinant expression often only have a very low stability in the sample solution and tend to aggregate. A further disadvantage is that it is often not possible to selectively and reproducibly introduce marker groups into such polypeptides.

Moreover the production of recombinant polypeptide antigens involves high costs and large variations in the immunological reactivity in different lots of the recombinant polypeptide antigens can occur.

The object of the present invention was therefore to provide a process with which antigens for immunological tests can be produced in a simple and efficient manner wherein the disadvantages of the antigens known from the state of the art are at least partially eliminated. In addition the process should enable a selective and reproducible introduction of marker groups into the antigens.

This object is achieved by a process for the production of hapten-labelled peptides which is characterized in that (a) a peptide with the desired amino acid sequence is synthesized on a solid phase from amino acid derivatives whose reactive side groups are blocked by protecting groups wherein the protecting groups on primary amino side groups are selected in such a way that, if desired, they can be selectively cleaved off, (b) protecting groups are cleaved off to form at least one free primary amino group, (c) a hapten-active ester derivative is coupled to the at least one free primary amino group of the peptide and (d) if desired protecting groups that still remain are cleaved off the hapten being selected from the group comprising sterols, bile acids, sexual hormones, corticoids, cardenolides, cardenolide-glycosides, bufadienolides, steroid-sapogenines and steroid alkaloids.

The peptides produced by the process according to the invention preferably have a maximum length of 50 amino acids, particularly preferably of 30 amino acids and are excellently suitable for immunological methods of detection and in particular for the determination of specific immunoglobulins. Surprisingly it was found that the peptides produced by the process according to the invention have a high affinity and specificity for the immunoglobulins to be detected despite the presence of bulky hapten marker groups.

The process according to the invention enables hapten marker groups to be introduced selectively with regard to their location as well as with regard to their number. In the peptide synthesis according to the invention it is namely possible by using particular protecting groups on primary amino groups of the amino acid derivatives used to specifically select those positions on the peptide which will be available for reaction with the hapten after selective cleavage of protecting groups. In this manner an improved reproducibility and sensitivity of the test is achieved.

A further advantage of the process according to the invention is that the use of peptide antigens enables all antibody classes such as IgG, IgN, IgE and IgA to be recognized. Also the test is less susceptible to interference by using defined small and stable antigens which do not tend to aggregate.

The haptens that are coupled by the process according to the invention to the peptide are molecules with a steroid backbone that are selected from the group comprising sterols, bile acids, sexual hormones, corticoids, cardenolides, cardenolide-glycosides, bufadienolides, steroid-sapogenines and steroid alkaloids. These haptens are capable of binding to a specific receptor, e.g. to antibodies or antibody fragments which are directed against the hapten. The hapten is particularly preferably selected from the group comprising cardenolides and cardenolide-glycosides. Representatives of these substance classes are digoxigenin, digitoxigenin, gitoxigenin, strophanthidin, digoxin, digitoxin, ditoxin and strophanthin, digoxigenin and digoxin being particularly preferred.

In the process according to the invention the hapten-active ester derivative is coupled to the amino terminus or/and to free primary amino side groups of the peptide. The term "active ester" within the sense of the present invention encompasses activated ester groups that can react with free amino groups of peptides under such conditions that no interfering side reactions with other reactive groups of the peptide can occur. An N-hydroxysuccinimide ester is preferably used as the active ester derivative. Examples of suitable hapten-active ester derivatives are digoxin-4'''-hemiglutarate-N-hydroxysuccinimide ester, digoxigenin-3-carboxymethyl ether-N-hydroxysuccinimide ester, digoxigenin-3-O-methyl-carbonyl-ε-aminocaproic acid-N-hydroxysuccinimide ester, digoxigenin-3-hemisuccinate-N-hydroxysuccinimide ester, digitoxin-4'''-hemiglutarate-N-hydroxysuccinimide ester and digitoxigenin-3-hemisuccinate-N-hydroxysuccinimide ester. These hapten derivatives are commercially available from the Boehringer Mannheim Company GmbH (Mannheim, GER). In addition to the N-hydroxysuccinimide esters it is also possible to use analogous p-nitro-phenyl, pentafluorophenyl, imidazolyl or N-hydroxybenzotriazolyl esters.

In the process according to the invention the peptide having the desired amino acid sequence is synthesized on a solid phase preferably using a commercial peptide synthesizer (e.g. the instruments A 431 or A 433 from Applied Biosystems). The synthesis is carried out according to known methods preferably starting at the carboxyl terminus of the peptide using amino acid derivatives. Amino acid derivatives are preferably used whose amino terminal group required for coupling is derivatized with a fluorenylmethyloxycarbonyl (Fmoc) residue. Reactive side groups of the amino acids used contain protecting groups that can be readily cleaved off after completion of the peptide synthesis. Preferred examples of this are protecting groups such as triphenylmethyl (Trt), t-butyl ether (tBu), t-butyl ester (O tBu), tert.-butoxycarbonyl (Boc) or 2,2,5,7,8-pentamethylchroman-6-sulfonyl (Pmc). The amino side chains of lysine residues or of other amino acid derivatives with primary amino side groups that are located at positions of the peptide which are later intended to be derivatized with the hapten are provided with a first amino protecting group which is selected such that it can be quantitatively cleaved off under particular reaction conditions e.g. in the presence of acid. An example of a suitable acid-labile protecting group is Boc. The side groups of lysine residues or of other amino acid residues with primary amino side groups to which no coupling of a hapten is desired are provided with a second amino-protecting group which is selected such that it cannot itself be cleaved off under conditions under which the first protecting group can be cleaved off. The second protecting group is also preferably stable under those conditions under which the peptide is cleaved from the solid phase and under which all other protecting groups are cleaved off. Examples of such second protecting groups are acid-resistant protecting groups such as phenylacetyl. In addition to the 20 natural amino acids the peptide can also contain artificial amino acids such as β-alanine, γ-aminobutyric acid, ε-amino-caproic acid, norleucine or ornithine. These artificial amino acids are used for the synthesis in a protected form analogously to the natural amino acids.

After completion of the synthesis protecting groups, including the first amino-protecting groups, which are located at the positions at which the coupling of the hapten is to take place are cleaved, optionally after releasing the peptide from the solid phase. Then the product obtained in this manner is purified, preferably by HPLC. Subsequently the hapten label is introduced by reacting the peptide with the hapten-active ester derivative desired in each case which reacts with free primary amino groups i.e. with the amino terminal group or/and amino side groups of the peptide. Preferably 1.5 to 2.5 equivalents of active ester are used per free primary amino group. Subsequently the reaction product is purified, preferably by HPLC.

If the peptide still contains amino groups that are derivatized with a second protecting group such as phenylacetyl then these protecting groups are removed in the last step. Phenylacetyl protecting groups can for example be enzymatically removed at room temperature with immobilized or soluble penicillin G amidase in aqueous solution containing an organic solvent.

If the peptides produced by the process according to the invention contain an intramolecular disulfide bridge, then the peptide sequence can be oxidized on the solid phase with for example iodine in hexafluoroisopropanol/dichloromethane (Kamber and Hiskey in Gross E. and Meienhofer J., The Peptides, Academic Press, New York, 1981, pages 145 to 147) after completion of the synthesis but before cleaving the N-terminal Fmoc-protecting group of the last amino acid, and subsequently the N-terminal Fmoc-protecting group is cleaved.

A peptide is preferably synthesized which comprises an immunologically reactive epitope region, i.e. an antibody-binding peptide sequence, and a spacer region. In this case at least one hapten label is preferably coupled to the spacer region. Peptides in which the label is located in the spacer region often have a better sensitivity in immunological tests.

The spacer region which preferably has a length of 1 to 10 amino acids has a stabilizing and solubilizing effect since it preferably contains charges or/and can form hydrogen bridges. In addition it can sterically facilitate the binding of several, e.g. high molecular receptors, to the hapten-labelled peptide. The amino acids of the spacer region are preferably selected from the group comprising glycine, β-alanine, γ-aminobutyric acid, ε-aminocaproic acid, lysine and compounds having the structural formula $NH_2$—$[(CH_2)_nO]_x$—$CH_2$—$CH_2$—$COOH$ in which n is 2 or 3 and x is 1 to 10. In addition the spacer region preferably contains at least some artificial amino acid derivatives. The spacer region is preferably located at the amino terminus or/and at the carboxy terminus of the peptide.

Peptides are preferably synthesized by the process according to the invention which contain an epitope region from pathogenic organisms e.g. bacteria, viruses and protozoa or from autoimmune antigens. The immunologically reactive epitope region is preferably derived from viral antigens e.g. the amino acid sequences of HIV I, HIV II, HIV subtype O or hepatitis C virus (HCV).

Preferably HIV I, HIV II or HIV subtype O epitopes are selected from the regions gp32, gp41 and gp120. HCV epitopes are preferably selected from the Core/Env region of the non-structural protein regions NS3, NS4 or NS5.

The epitope region of HIV I, HIV II or HIV subtype O amino acid sequences is particularly preferably selected from the group of amino acid sequences:

NNTRKSISIG PGRAFYT (I) SEQ ID NO. 1
NTTRSISIGP GRAFYT (II) SEQ ID NO. 2
IDIQEERRMR IGPGMAWYS (III) SEQ ID NO. 3
QARILAVERY LKDQQLLGIW GASG (IV) SEQ ID NO. 4
LGIWGCSGKL ICTTAVPWNA SWS (V) SEQ ID NO. 5
KDQQLLGIWG SSGKL (VI) SEQ ID NO. 6
ALETLLQNQQ LLSLW (VII) SEQ ID NO. 7
LSLWGCKGKL VCYTS (VIII) SEQ ID NO. 8

WGIRQLRARL LALETLLQN (IX) SEQ ID NO. 9 and

QAQLNSWGCA FRQVCHTTVP WPNDSLT (X) SEQ ID NO. 10 or partial sequences thereof which have a length of at least 6 and preferably of at least 8 amino acids.

The amino acid sequences I to III are derived from the gp120 region of HIV I, the amino acid sequences IV to IX are derived from the gp41 region of HIV I and the amino acid sequence X is derived from the gp32 region of HIV II. The amino acid sequences I to X are also shown in the sequence protocols SEQ ID NO. 1 to SEQ ID NO. 10. Each of the sequences V, VIII and X contain two cysteines which are preferably present in the form of a disulfide bridge. These sequences preferably contain an N-terminal or/and a C-terminal spacer as defined above which carries a hapten label, preferably a digoxigenin or digoxin label and particularly preferably a digoxigenin-3-carboxy-methyl ether label. Lysine residues located within the epitope region can also optionally be present in a labelled form.

The epitope region of HCV amino acid sequences is preferably selected from the group of the amino acid sequences:

SRRFAQALPV WARPD (XI) SEQ ID NO. 11

PQDVKFPGGG QIVGGV (XII) SEQ ID NO. 12

EEASQHLPYI EQ (XIII) SEQ ID NO. 13

QKALGLLQT (XIV) SEQ ID NO. 14

SRGNHVSPTH YVPESDAA (XV) SEQ ID NO. 15

PQRKNKRNTN RRPQDVKFPG GGQIVGVV (XVI) SEQ ID NO. 16 and

AWYELTPAET TVRLRAYMNT PGLPV (XVII) SEQ ID NO. 17 or partial sequences thereof which have a length of at least 6 and preferably at least 8 amino acids. The sequence XI is derived from the NS5 region, the sequences XII and XVI from the Core region, the sequences XIII, XIV and XV from the NS4 region and the sequence XVII is derived from the NS3 region of HCV. The amino acid sequences XI to XVII are shown in the sequence protocols SEQ ID NO. 11 to SEQ ID NO. 17. Peptides with the above-mentioned epitopes preferably contain an additional spacer region which carries a hapten label.

A further subject matter of the present invention is a hapten-labelled peptide which has a maximum length of 50 and preferably of 30 amino acids and whose amino terminus or/and amino side groups are coupled with at least one hapten-active ester derivative. The hapten is preferably digoxigenin or digoxin and the active ester is preferably a N-hydroxysuccinimide ester.

The peptide according to the invention preferably comprises an immunologically reactive epitope region that can react with antibodies from for example human sera and an immunologically non-reactive spacer region wherein the spacer region carries at least one hapten label. The spacer region is preferably located at the amino terminus of the peptide and has a length of 1 to 10 amino acids. The epitope region is preferably derived from the amino acid sequences of HIV I, HIV II or HCV including variants e.g. subtypes thereof e.g. HIV subtype O and is one of the amino acid sequences I to XVII or a partial sequence thereof.

The present invention also concerns the use of hapten-labelled peptides as antigens in an immunological method for the determination of specific antibodies in a sample liquid. Such antibodies are preferably determined which indicate an infection by microorganisms such as bacteria, viruses or protozoa. Antibodies directed against viruses e.g. antibodies directed against HIV or hepatitis viruses are particularly preferably determined. The sample liquid is preferably serum and particularly preferably human serum. In addition it is preferred that the hapten-labelled peptides according to the invention are used in an immunological method in a bridge test format.

The present invention also concerns a method for the immunological determination of a specific antibody in a sample liquid which is characterized in that the sample liquid is incubated with (a) a first labelled antigen which is directed against the antibody to be determined and comprises a hapten-labelled peptide as defined above and (b) a receptor for the hapten which carries a signal-generating group and the antibody is detected by means of a binding to the peptide. A peptide labelled with digoxin or digoxigenin is preferably used as the first antigen and an antibody directed against digoxigenin or/and digoxin is preferably used as the receptor. The term “antibody” in this connection is intended to also encompass antibody fragments e.g. Fab, Fab', $F(ab)_2$, $F(ab')_2$ fragments or other antibody fragments e.g. modified by genetic engineering. The receptor is coupled to a signal-generating group, preferably an enzyme such as peroxidase, alkaline phosphatase, β-galactosidase, urease or Q-β-replicase. However, the signal-generating group can also be a chromogenic, radioactive or NMR-active group or a metal particle (e.g. gold). The signal-generating group is preferably an enzyme.

The immunological method of determination according to the invention can in fact be carried out according to any known test format e.g. in a homogeneous immunoassay with a single reaction phase or in a heterogeneous immunoassay with more than one reaction phase. A heterogeneous test format is preferably used in which the presence of the antibody is detected in the presence of a solid phase. One embodiment of this test format is the so-called double antigen bridge test design. In this case the sample liquid is incubated in the presence of a solid phase with the first antigen and with a second antigen which is directed against the antibody to be determined and (a) is bound to the solid phase or (b) is present in a form capable of binding to the solid phase. The antibody to be determined in the sample liquid is detected by determining the label in the solid phase or/and in the liquid phase. The second antigen is preferably labelled with biotin and is capable of binding to a solid phase which is coated with streptavidin or avidin. A peptide labelled with biotin is preferably used as the second antigen.

The test procedure preferably comprises mixing the sample liquid with the first antigen and the second antigen on the solid phase in order to obtain a labelled immobilized complex of first antigen, antibody and solid phase-bound second antigen. Compared to other test formats for detecting antibodies, the bridge test format leads to an improvement in sensitivity i.e. all immunoglobulin classes such as IgG, IgM, IgA and IgE are recognized as well as in specificity i.e. the unspecific reactivity is reduced. The specificity and sensitivity of the double antigen bridge test can be further improved if a two step test procedure is used in which the sample liquid is mixed with the first and the second antigen in a first step and subsequently the receptor for the hapten label of the first antigen which carries the signal-generating group is added.

A further advantage of the double antigen bridge test format in which a solid phase-bound and a hapten-labelled peptide are used as antigens is that it is possible to reduce the risk of a false negative evaluation of samples which have a high titre of the antibody to be determined as a result of the Hook effect and namely by increasing the number of marker groups per peptide to preferably 2 to 10 marker groups. Increasing the number of hapten marker groups per peptide leads to an improvement of the Hook sensitivity compared to test procedures with directly detectable marker groups as a result of the amplification of the signal by means of the receptor.

Yet a further subject matter of the present invention is a reagent for the immunological determination of a specific antibody which contains at least one hapten-labelled peptide according to the invention which reacts with the antibody to be determined. If the reagent is used in a double antigen bridge test, then it preferably contains (a) the hapten-labelled peptide, (b) a receptor for the hapten which carries a signal-generating group and (c) a further antigen which reacts with the antibody to be determined which is bound to a solid phase or is present in a form capable of binding to a solid phase. The hapten is preferably a cardenolide or cardenolide-glycoside, in particular digoxin or digoxigenin, the receptor for the hapten is preferably an antibody directed against the hapten, the signal-generating group is preferably an enzyme, the other antigen is preferably biotinylated and is capable of binding to a solid phase coated with streptavidin or avidin.

The present invention is further described by the following examples and sequence protocols.

SEQ ID NO. 1: shows the amino acid sequence of an epitope from the gp120 region of HIV I;

SEQ ID NO. 2: shows the amino acid sequence of a further epitope from the gp120 region of HIV I;

SEQ ID NO. 3: shows the amino acid sequence of a further epitope from the gp120 region of HIV I, subtype O;

SEQ ID NO. 4: shows the amino acid sequence of an epitope from the gp41 region of HIV I;

SEQ ID NO. 5: shows the amino acid sequence of a further epitope from the gp41 region of HIV I;

SEQ ID NO. 6: shows the amino acid sequence of yet a further epitope from the gp41 region of HIV I;

SEQ ID NO. 7: shows the amino acid sequence of an epitope from the gp41 region of HIV I, subtype O;

SEQ ID NO. 8: shows the amino acid sequence of a further epitope from the gp41 region of HIV I, subtype O;

SEQ ID NO. 9: shows the amino acid sequence of yet a further epitope from the gp41 region of HIV I, subtype O;

SEQ ID NO. 10: shows the amino acid sequence of an epitope from the gp32 region of HIV II;

SEQ ID NO. 11: shows the amino acid sequence of an epitope from the NS5 region of HCV;

SEQ ID NO. 12: shows the amino acid sequence of an epitope from the Core region of HCV;

SEQ ID NO. 13: shows the amino acid sequence of an epitope from the NS4 region of HCV;

SEQ ID NO. 14: shows the amino acid sequence of a further epitope from the NS4 region of HCV;

SEQ ID NO. 15: shows the amino acid sequence of yet a further epitope from the NS4 region of HCV;

SEQ ID NO. 16: shows the amino acid sequence of a further epitope from the Core region of HCV and SEQ ID NO. 17: shows the amino acid sequence of an epitope from the NS3 region of HCV.

EXAMPLE 1

Production of hapten-labelled peptides

The hapten-labelled peptides were synthesized by means of fluorenylmethyloxycarbonyl (Fmoc) solid phase peptide synthesis on a batch peptide synthesizer e.g. from Applied Biosystems A431 or A433. For this 4.0 equivalents of each of the amino acid derivatives shown in table 1 were used:

TABLE 1

| | |
|---|---|
| A | Fmoc-Ala—OH |
| C | Fmoc-Cys (Trt)—OH |
| D | Fmoc-Asp(OtBu)—OH |
| E | Fmoc-Glu(OtBu)—OH |
| F | Fmoc-Phe—OH |
| G | Fmoc-Gly—OH |
| H | Fmoc-His(Trt)—OH |
| I | Fmoc-Ile—OH |
| K1 | Fmoc-Lys(phenylacetyl)-OH |
| K2 | Fmoc-Lys (BOC)—OH |
| K3 | Fmoc-Lys (Fmoc)—OH |
| L | Fmoc-Leu—OH |
| M | Fmoc-Met—OH |
| N | Fmoc-Asn(Trt)-OH |
| P | Fmoc-Pro—OH |
| Q | Fmoc-Gln(Trt)—OH |
| R | Fmoc-Arg(Pmc)—OH |
| S | Fmoc-Ser(tBu)—OH |
| T | Fmoc-Thr(tBu)—OH |
| U | Fmoc-βAlanine—OH |
| V | Fmoc-Val—OH |
| W | Fmoc-Trp—OH |
| Y | Fmoc-Tyr(tBu)—OH |
| Z | Fmoc-ε-aminocaproic acid-OH |
| Nle | Fmoc-ε-norleucine-OH |
| Abu | Fmoc-γ-aminobutyric acid-OH |

The lysine derivative K1 was used for positions at which it was not intended to introduce a hapten label. The lysine derivative K2 was used for positions at which it was intended to introduce a hapten label. The lysine derivative K3 was used to couple the ε-amino group to the spacer region of the peptide.

The amino acids or amino acid derivatives were dissolved in N-methylpyrrolidone. The peptide was synthesized on 400–500 mg 4-(2',4'-dimethoxyphenyl-Fmoc-aminomethyl)-phenoxy resin (Tetrahedron Letters 28 (1987), 2107) with a loading of 0.4–0.7 mmol/g (JACS 95 (1973), 1328). The coupling reactions were carried out for 20 minutes in dimethylformamide as a reaction medium with 4 equivalents dicyclohexylcarbodiimide and 4 equivalents of N-hydroxybenzotriazole relative to the Fmoc-amino acid derivative. The Fmoc group was cleaved in 20 minutes after each synthesis step using 20% piperidine in dimethylformamide.

If cysteine residues are present in the peptide sequence, an oxidation on the solid phase is carried out immediately after completion of the synthesis using iodine in hexafluoroisopropanol/dichloromethane.

The release of the peptide from the synthesis resin and the cleavage of the acid-labile protecting groups—with the exception of the phenylacetyl protecting group—was achieved in 40 min at room temperature with 20 ml trifluoro acetic acid, 0.5 ml ethanedithiol, 1 ml thioanisole, 1.5 g phenol and 1 ml water. The reaction solution was subsequently admixed with 300 ml cooled diisopropyl ether and kept at 0° C. for 40 min to completely precipitate the peptide. The precipitate was filtered, washed again with diisopropyl ether, dissolved in a small amount of 50% acetic acid and lyophilized. The crude material obtained was purified in ca. 120 min. by means of preparative HPLC on delta-PAK RP C18 material (column 50×300 mm, 100Å, 15μ) using an appropriate gradient (eluant A: water, 0.1% trifluoroacetic acid, eluant B: acetonitrile, 0.1% trifluoroacetic acid). The identity of the eluted material was checked by means of ion spray mass spectrometry.

The hapten label, e.g. a digoxigenin or digoxin label, was introduced in solution using appropriate active ester derivatives and the free amino groups of the peptide. The peptide to be derivatized was dissolved in a mixture of DMSO and 0.1 M potassium phosphate buffer pH 8.5. Subsequently 2 equivalents of active ester per free primary amino function dissolved in a small amount of DMSO was added dropwise and stirred at room temperature. The reaction was monitored by means of analytical HPLC. The product is purified by means of preparative HPLC.

If the peptide still contained lysines protected with phenylacetyl, then this protecting group was enzymatically cleaved at room temperature in the last step using penicillin G amidase in an aqueous medium containing a proportion of organic solvent. The enzyme was separated e.g. by filtration and the peptide was purified by means of preparative HPLC. The identity of the eluted material was checked by means of ion spray mass spectrometry.

The peptide compounds shown in Table 2 derived from the regions gp120, gp41 and gp32 of HIV I and HIV II were prepared using digoxigenin-3-carboxymethyl ether-N-hydroxysuccinimide ester (Boehringer Mannheim GmbH, Mannheim, GER).

or in the sequence using a biotin-ε-derivatized lysine residue (Fmoc-Lys (biotin)-OH).

EXAMPLE 2

Improvement of specificity and sensitivity by a preferred test procedure

The specificity and sensitivity of a double antigen bridge test using the peptides according to the invention can also be improved by a test procedure in which the sample, the hapten-labelled antigen and the solid phase antigen are mixed in a first step and subsequently, preferably after 1 to 4 h, particularly preferably after 1.5 to 2.5 h, the anti-hapten antibody is added.

The HIV epitopes gp41/1 and gp41/2 (Table 2) were used as antigens.

The test conditions for the preferred two step test were as follows:

50 mmol/l neutral potassium phosphate buffer, pH 7.2, 0.2% bovine serum albumin (BSA), 0.2% sodium laurylsulfate (SLS) detergent incubation times incubation of hapten-labelled and solid phase antigen with serum: 120 min incubation with conjugate of anti-digoxigenin antibody and peroxidase (<Dig>-POD) 60 min incubation with 2,2'-azino-di-[3-ethylbenzylthiazoline-sulfonate(6)] ABTS): 60 min incubation temperature: 25° C.

TABLE 2

| | |
|---|---|
| gp120 | digoxigenin-3-cme-UZU-NNTRKSISIGPGRAFYT SEQ ID NO.18 |
| | digoxigenin-3-cme-UZ-NTTRSISIGPGRAFY SEQ ID NO.19 |
| | digoxigenin-3-cme-UZU-IDIQEERRMRIGPGMAWYS SEQ ID NO.20 |
| gp41/1 | digoxigenin-3-cme-UZU-AVERYLKDQQLLGIW SEQ ID NO.21 |
| | digoxigenin-3-cme-ZUZU-AVERYLKDQQLLGIW SEQ ID NO.22 |
| | digoxigenin-3-cme-UZ-QARILAVERYLKDQQLLGIWGASG SEQ ID NO.23 |
| | digoxigenin-3-cme-ZGGGG-QARILAVERYLKDQQLLGIWGASG SEQ ID NO.24 |
| | digoxigenin-3-cme-UZU-WGIRQLRARLLALETLLQN SEQ ID NO.25 |
| gp41/2 | digoxigenin-3-cme-UZU-LGIWGCSGKLICTTAV |
| | LGIWGCSGK-(cme-3-digoxigenin)-LICTTAV SEQ ID NO.26 |
| | digoxigenin-3-cme-UZU-LGIWGCSGK-(cme-3-digoxigenin)-LICTTAV SEQ ID NO.27 |
| | digoxigenin-3-cme-ZU-GCSGKLICTTAVPWNASWS |
| | GCSGK-(cme-3-digoxigenin)-LICTTAVPWNASWS |
| | GCSGKLICTTAVPWNASWSK(cme-3-digoxigenin)G SEQ ID NO.28 |
| | digoxigenin-3-cme-UZU-LSLWGCKGKLVCYTS SEQ ID NO.29 |
| gp41/3 | digoxigenin-3-cme-UZU-KDQQLLGIWGSSGKL SEQ ID NO.30 |
| gp41/4 | digoxigenin-3-cme-UZU-ALETLLQNQLLSLW SEQ ID NO.31 |
| gp32 | digoxigenin-3-cme-Z-NSWGCAFRQVCHTT SEQ ID NO.32 |

The peptides shown in the following Table 3 were synthesized from the NS5 region, the NS4 region and the Core region of HCV.

bound/free separation between all incubation steps

The test conditions for the alternative two-step test were as follows:

TABLE 3

| | |
|---|---|
| NS5/1 | digoxigenin-3-cme-UZU-SRRFAQALPVWARPD SEQ ID NO.33 |
| Core2 | digoxigenin-3-cme-U-PQDVKFPGGGQIVGGV SEQ ID NO.34 |
| NS4/1 | digoxigenin-3-cme-UU-Nle-EEASQHLPYIEQ SEQ ID NO.35 |
| NS4/2 | digoxigenin-3-cme-UU-QKALGLLQT SEQ ID NO.36 |
| NS4/3 | digoxigenin-3-cme-UZU-SRGNHVSPTHYVPESDAA SEQ ID NO.37 |
| Core1 | digoxigenin-3-cme-UZU-KNKRNTNRR SEQ ID NO.38 |
| Core1 + 2 | digoxigenin-3-cme-U-PQRKNKRNTNRRPQDVKFPGGGQIVGVV SEQ ID NO.39 |
| NS3/1 | digoxigenin-3-cme-UZ-AWYELTPAETTVRLRAYMNTPGLPV SEQ ID NO.40 |

Biotin-labelled peptides were either synthesized N-terminally by derivatization on a resin (biotin active ester)

50 mmol/l neutral potassium phosphate buffer, pH 7.2, 0.2% BSA, 0.2% SLS detergent incubation times
incubation of solid phase antigen with serum: 90 min
incubation with hapten-labelled antigen and <Dig>-POD: 90 min
incubation with ABTS: 60 min
incubation temperature: 25° C.
bound/free separation between all incubation steps The test conditions for the one-step test were as follows:
50 mmol/l neutral potassium phosphate buffer, pH 7.2, 0.2% BSA, 0.2% SLS detergent
incubation times
incubation of both antigens with serum and <Dig>-POD: 120 min
incubation with ABTS: 60 min
incubation temperature: 25° C.
bound/free separation between all incubation steps The results of the test are shown in Table 4. It can be seen that a much higher signal differentiation, i.e. the ratio of the measured signals for positive samples to negative samples, is achieved in the preferred test procedure.

TABLE 4

| Sample number | Single-step test procedure | preferred two-step test procedure 1. mix sample and both specific antigens 2. add anti-hapten antibody for the detection reaction | alternative two step test procedure 1. mix sample and wall-bound specific antigen 2. add specific detection antigen and anti-hapten antibody for the detection reaction |
|---|---|---|---|
| A) negative samples | Signal in mA | Signal in mA | Signal in mA |
| 1 | 19 | 7 | 7 |
| 2 | 21 | 12 | 9 |
| 3 | 17 | 6 | 5 |
| 4 | 19 | 5 | 7 |
| 5 | 18 | 4 | 8 |
| 6 | 28 | 7 | 16 |
| 7 | 20 | 10 | 9 |
| 8 | 21 | 7 | 11 |
| 9 | 18 | 10 | 7 |
| 10 | 19 | 11 | 8 |
| 11 | 17 | 8 | 9 |
| 12 | 19 | 12 | 7 |
| 13 | 22 | 7 | 7 |

TABLE 4-continued

| | | | |
|---|---|---|---|
| 14 | 20 | 5 | 17 |
| 15 | 24 | 40 | 8 |
| 16 | 19 | 10 | 7 |
| 17 | 20 | 4 | 8 |
| 18 | 23 | 6 | 8 |
| 19 | 20 | 8 | 7 |
| 20 | 16 | 11 | 7 |
| B) Positive samples | Signal in mA | Signal in mA | Signal in mA |
| 1 | 405 | 2401 | 3681 |
| 2 | 1080 | 4836 | 4931 |
| 3 | 158 | 11oo | 300 |
| 4 | 760 | 6210 | 2155 |
| 5 | 1094 | 3578 | 1835 |
| 6 | 452 | 2296 | 2954 |
| 7 | 163 | 1068 | 136 |
| 8 | 76 | 195 | 14 |
| 9 | 2405 | 7803 | 2671 |
| 10 | 293 | 3093 | 575 |
| 11 | 303 | 2430 | 42 |
| 12 | 37 | 132 | 11 |
| 13 | 19 | 9 | 9 |
| 14 | 63 | 218 | 11 |
| 15 | 74 | 297 | 15 |
| 16 | 60 | 253 | 16 |
| 17 | 86 | 509 | 17 |
| 18 | 106 | 1182 | 22 |
| 19 | 962 | 8782 | 338 |
| 20 | 815 | 7335 | 167 |

EXAMPLE 3

A peptide antigen according to the invention was compared with a recombinant polypeptide antigen in a double antigen bridge test. In an example according to the invention the digoxigenylated peptide antigen gp41/2 (Table 2) was tested in combination with a biotinylated peptide antigen of the same sequence. In a comparative example a digoxigenylated polypeptide antigen rec. gp41 (Chang et al., Science 228 (1985), 93–96) was tested in combination with a biotinylated polypeptide of the same sequence.

The results of the test are shown in Table 5. "NC" denotes negative control, "PC" denotes positive control. The "cut-off" index is the border between a positive and negative evaluation of an experiment. It is defined as 2×NC. It is apparent from Table 5 that almost no differentiation between negative and positive samples is possible with the recombinant polypeptide antigen whereas the peptide antigen allows a very good differentiation.

TABLE 5

| Sample (dilution) | rec.gp41-Bi/Dig Absorbance | peptide gp41-Bi/Dig Absorbance | rec.gp41-Bi/Dig cut-off index | peptide gp41-Bi/Dig cut-off index |
|---|---|---|---|---|
| NC | 768 | 36 | 0.5 | 0.5 |
| PC | 3066 | 2094 | 2.0 | 29.1 |
| PC 1:2 | 2587 | 1410 | 1.7 | 19.6 |
| PC 1:4 | 1681 | 867 | 1.1 | 12.0 |
| positive 1 | 1466 | 9999 | 1.0 | 138.9 |
| positive 2 | 497 | 9999 | 0.3 | 138.9 |
| positive 3 | 801 | 9999 | 0.4 | 138.9 |
| positive 4 | 1213 | 9999 | 0.8 | 138.9 |
| positive 5 | 952 | 8039 | 0.6 | 111.7 |
| negative 1 | 738 | 50 | 0.5 | 0.7 |
| negative 2 | 769 | 39 | 0.5 | 0.6 |
| negative 3 | 747 | 40 | 0.5 | 0.5 |

We claim:

1. A process for producing a hapten-labelled peptide, comprising:
(a) synthesizing a peptide with a predetermined amino acid sequence on a solid phase from a plurality of amino acid derivatives containing a plurality of primary amino groups, wherein at least one first primary amino group is blocked by a first amino protecting group and at least one second primary amino group is blocked by a second amino protecting group which cannot be cleaved off under conditions under which the first protecting group can be cleaved off, wherein the second amino protecting group is phenylacetyl;

(b) cleaving off the first amino protecting group to produce at least one free primary amino group;

(c) before or after step (b), releasing the peptide from the solid phase;

(d) coupling a hapten-active ester derivative with the at least one free primary amino group, wherein the hapten is selected from the group consisting of sterols, bile acids, sexual hormones, corticoids, cardenolides, cardenolide-glycosides, bufadienolides, steroid-sapogenines and steroid alkaloids; and (e) cleaving off the second amino protecting group.

2. The process as claimed in claim 1, wherein the at least one first primary amino group comprises a plurality of first primary amino groups.

3. The process as claimed in claim 1, wherein the at least one second primary amino group comprises a plurality of second primary amino groups.

4. The process as claimed in claim 1, wherein the hapten is selected from the group consisting of cardenolides and cardenolide-glycosides.

5. The process as claimed in claim 4, wherein the hapten is selected from the group consisting of digoxigenin, digitoxigenin, gitoxigenin, strophanthidin, digoxin, digitoxin, ditoxin and strophanthin.

6. The process as claimed in claim 5, wherein the hapten is selected from the group consisting of digoxigenin and digoxin.

7. The process as claimed in claim 1, wherein the first amino protecting group is acid-labile.

8. The process as claimed in claim 1, wherein the active ester derivative is an N-hydroxysuccinimide ester.

9. The process as claimed in claim 1, wherein the peptide comprises an immunologically reactive epitope and a spacer region, and wherein at least one free primary amino group coupled with the hapten-active ester is located in the spacer region.

10. The process as claimed in claim 9, wherein the spacer region has a length of 1 to 10 amino acids.

11. The process as claimed in claim 9, wherein a spacer region is located at at least one of the amino terminus and the carboxy terminus of the peptide.

12. The process as claimed in claim 9, wherein the spacer region contains amino acids which either have charges, can form hydrogen bridges, or both.

13. The process as claimed in claim 9, wherein the spacer region contains at least one amino acid each independently selected from the group consisting of glycine, β-alanine, γ-aminobutyric acid, ε-aminocaproic acid, lysine and a compound having the structural formula:

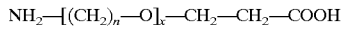

$$NH_2-[(CH_2)_n-O]_x-CH_2-CH_2-COOH$$

wherein n is 2 to 3 and x is 1 to 10.

14. The process as claimed in claim 1, wherein the peptide comprises an epitope region from HIV I, HIV II or HCV.

15. The process as claimed in claim 14, wherein the epitope region is selected from the group of HIV I or HIV II amino acid sequences consisting of SEQ ID NO. 1 through SEQ ID NO. 10, or a partial sequence thereof which has a length of at least 6 amino acids.

16. The process as claimed in claim 14, wherein the epitope region is selected from the group of HCV sequences consisting of SEQ ID NO. 11 through SEQ ID NO. 17, or a partial sequence thereof which has a length of at least 6 amino acids.

17. A hapten-labelled peptide, comprising a spacer region and an immunologically reactive epitope region, wherein at least one first primary amino group is located in a predetermined position of the spacer region and the first primary amino group has a hapten-active ester derivative coupled therewith, and at least one second primary amino group is located in the immunologically reactive epitope region and is free of hapten labelling.

18. The peptide as claimed in claim 17, wherein the hapten is selected from the group consisting of digoxigenin and digoxin.

19. The peptide as claimed in claim 17, wherein a spacer region is located at at least one of the amino terminus and the carboxy terminus of the peptide.

20. The peptide as claimed in claim 17, wherein the peptide comprises an epitope region from HIV I, HIV II or HCV.

21. The peptide as claimed in claim 20, wherein the epitope region is selected from the group of HIV I or HIV II amino acid sequences consisting of SEQ ID NO. 1 through SEQ ID NO. 10, or a partial sequence thereof which has a length of at least 6 amino acids.

22. The peptide as claimed in claim 20, wherein the epitope region is selected from the group of HCV sequences consisting of SEQ ID NO. 11 through SEQ ID NO. 17, or a partial sequence thereof which has a length of at least 6 amino acids.

23. In an immunological method for determining an antibody in a sample in the bridge test format, the improvement comprising incubating the sample with the peptide as claimed in claim 17.

24. A method for immunologically determining an antibody in a sample liquid, the method comprising:
  (a) incubating the sample liquid with
    (1) a first labelled antigen which is directed against the antibody to be determined, the first labelled antigen comprising a hapten-labelled peptide as claimed in claim 17, and
    (2) a receptor for the hapten, wherein the receptor carries a signal-generating group,
  (b) binding the antibody to the peptide to produce a bound antibody; and
  (c) determining the bound antibody.

25. The method as claimed in claim 24, wherein the hapten is selected from the group consisting of digoxigenin and digoxin and the receptor is an antibody directed against the hapten.

26. The method as claimed in claim 24, wherein in step (a) the sample liquid is incubated in the presence of a solid phase and additionally incubated with a second antigen which is directed against the antibody to be determined and (1) is bound to the solid phase or (2) is capable of binding to the solid phase, and wherein in step (c) the bound antibody is determined by detecting at least one of the first labelled antigen and the second antigen.

27. The method as claimed in claim 26, wherein the second antigen comprises biotin, and the solid phase is coated with streptavidin or avidin.

28. The method as claimed in claim 27, wherein the second antigen comprises a peptide labelled with biotin.

29. The method as claimed in claim 26, wherein the sample liquid is first incubated with the first labelled antigen and the second antigen and thereafter the receptor for the hapten is added.

30. A reagent for immunologically determining an antibody, comprising at least one hapten-labelled peptide as claimed in claim 17, wherein the peptide is directed against the antibody to be determined.

31. The reagent as claimed in claim 30, further comprising a receptor for the hapten, wherein the receptor carries a signal-generating group, and a further antigen which is directed against the antibody to be determined and (1) is bound to a solid phase or (2) is capable of binding to the solid phase.

* * * * *

SEQUENCE LISTING ( 1 ) GENERAL INFORMATION:

( i i i ) NUMBER OF SEQUENCES: 40

( 2 ) INFORMATION FOR SEQ ID NO: 1:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( i i i ) HYPOTHETICAL: No ( v i ) ORIGINAL SOURCE:
        ( A ) ORGANISM: Human immunodeficiency virus type 1

( v i i i ) POSITION IN GENOME:
        ( A ) CHROMOSOME/SEGMENT: gp120

( x i ) SEQUENCE DESCRIPTION: SEQ ID NO: 1:

```
Asn  Asn  Thr  Arg  Lys  Ser  Ile  Ser  Ile  Gly  Pro  Gly  Arg  Ala  Phe  Tyr
 1              5                        10                            15
Thr
```

( 2 ) INFORMATION FOR SEQ ID NO: 2:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( i i i ) HYPOTHETICAL: No ( v i ) ORIGINAL SOURCE:
        ( A ) ORGANISM: Human immunodeficiency virus type 1

( v i i i ) POSITION IN GENOME:
        ( A ) CHROMOSOME/SEGMENT: gp120

( x i ) SEQUENCE DESCRIPTION: SEQ ID NO: 2:

```
Asn  Thr  Thr  Arg  Ser  Ile  Ser  Ile  Gly  Pro  Gly  Arg  Ala  Phe  Tyr  Thr
 1              5                        10                            15
```

( 2 ) INFORMATION FOR SEQ ID NO: 3:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: peptide ( i i i ) HYPOTHETICAL: No ( v i ) ORIGINAL SOURCE:
        ( A ) ORGANISM: Human immunodeficiency virus type 1
        ( B ) STRAIN: subtype O ( v i i i ) POSITION IN GENOME:
        ( A ) CHROMOSOME/SEGMENT: gp120

( x i ) SEQUENCE DESCRIPTION: SEQ ID NO: 3:

```
Ile  Asp  Ile  Gln  Glu  Glu  Arg  Arg  Met  Arg  Ile  Gly  Pro  Gly  Met  Ala
 1              5                        10                            15
Trp  Tyr  Ser
```

( 2 ) INFORMATION FOR SEQ ID NO: 4:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: peptide ( i i i ) HYPOTHETICAL: No ( v i ) ORIGINAL SOURCE:
        ( A ) ORGANISM: Human immunodeficiency virus type 1

( v i i i ) POSITION IN GENOME:
        ( A ) CHROMOSOME/SEGMENT: gp41

( x i ) SEQUENCE DESCRIPTION: SEQ ID NO: 4:

```
Gln Ala Arg Ile Leu Ala Val Glu Arg Tyr Leu Lys Asp Gln Gln Leu
1               5                   10                  15
Leu Gly Ile Trp Gly Ala Ser Gly
            20
```

( 2 ) INFORMATION FOR SEQ ID NO: 5:

( i ) SEQUENCE CHARACTERISTICS:
        ( A ) LENGTH: 23 amino acids
        ( B ) TYPE: amino acid
        ( D ) TOPOLOGY: linear ( i i ) MOLECULE TYPE: peptide ( i i i ) HYPOTHETICAL: No ( v i ) ORIGINAL SOURCE:
        ( A ) ORGANISM: Human immunodeficiency virus type 1

( v i i i ) POSITION IN GENOME:
        ( A ) CHROMOSOME/SEGMENT: gp41

( x i ) SEQUENCE DESCRIPTION: SEQ ID NO: 5:

```
Leu Gly Ile Trp Gly Cys Ser Gly Lys Leu Ile Cys Thr Thr Ala Val
1               5                   10                  15
Pro Trp Asn Ala Ser Trp Ser
            20
```

( 2 ) INFORMATION FOR SEQ ID NO: 6:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i i i ) HYPOTHETICAL: No ( v i ) ORIGINAL SOURCE:
        ( A ) ORGANISM: Human immunodeficiency virus type 1

( v i i i ) POSITION IN GENOME:
        ( A ) CHROMOSOME/SEGMENT: gp41

( x i ) SEQUENCE DESCRIPTION: SEQ ID NO: 6:

```
Lys Asp Gln Gln Leu Leu Gly Ile Trp Gly Ser Ser Gly Lys Leu
1               5                   10                  15
```

( 2 ) INFORMATION FOR SEQ ID NO: 7:

( i ) SEQUENCE CHARACTERISTICS:

(A) LENGTH: 15 amino acids
(B) TYPE: amino acid
(D) TOPOLOGY: linear (ii) MOLECULE TYPE: peptide (iii) HYPOTHETICAL: No (vi) ORIGINAL SOURCE:
(A) ORGANISM: Human immunodeficiency virus type 1
(B) STRAIN: subtype O (viii) POSITION IN GENOME:
(A) CHROMOSOME/SEGMENT: gp41

(xi) SEQUENCE DESCRIPTION: SEQ ID NO: 7:

```
Ala Leu Glu Thr Leu Leu Gln Asn Gln Gln Leu Leu Ser Leu Trp
1               5                   10                  15
```

(2) INFORMATION FOR SEQ ID NO: 8:

(i) SEQUENCE CHARACTERISTICS:
(A) LENGTH: 15 amino acids
(B) TYPE: amino acid
(D) TOPOLOGY: linear (ii) MOLECULE TYPE: peptide (iii) HYPOTHETICAL: No (vi) ORIGINAL SOURCE:
(A) ORGANISM: Human immunodeficiency virus type 1
(B) STRAIN: subtype O (viii) POSITION IN GENOME:
(A) CHROMOSOME/SEGMENT: gp41

(xi) SEQUENCE DESCRIPTION: SEQ ID NO: 8:

```
Leu Ser Leu Trp Gly Cys Lys Gly Lys Leu Val Cys Tyr Thr Ser
1               5                   10                  15
```

(2) INFORMATION FOR SEQ ID NO: 9:

(i) SEQUENCE CHARACTERISTICS:
(A) LENGTH: 19 amino acids
(B) TYPE: amino acid
(D) TOPOLOGY: linear (ii) MOLECULE TYPE: peptide (iii) HYPOTHETICAL: No (vi) ORIGINAL SOURCE:
(A) ORGANISM: Human immunodeficiency virus type 1
(B) STRAIN: subtype O (viii) POSITION IN GENOME:
(A) CHROMOSOME/SEGMENT: gp41

(xi) SEQUENCE DESCRIPTION: SEQ ID NO: 9:

```
Trp Gly Ile Arg Gln Leu Arg Ala Arg Leu Leu Ala Leu Glu Thr Leu
1               5                   10                  15
Leu Gln Asn
```

(2) INFORMATION FOR SEQ ID NO: 10:

(i) SEQUENCE CHARACTERISTICS:
(A) LENGTH: 27 amino acids
(B) TYPE: amino acid
(D) TOPOLOGY: linear (ii) MOLECULE TYPE: peptide (i i i) HYPOTHETICAL: No (v i) ORIGINAL SOURCE:
    (A) ORGANISM: Human immunodeficiency virus type 2

(v i i i) POSITION IN GENOME:
    (A) CHROMOSOME/SEGMENT: gp32

(x i) SEQUENCE DESCRIPTION: SEQ ID NO: 10:

```
Gln Ala Gln Leu Asn Ser Trp Gly Cys Ala Phe Arg Gln Val Cys His
1               5                   10                  15
Thr Thr Val Pro Trp Pro Asn Asp Ser Leu Thr
                20              25
```

(2) INFORMATION FOR SEQ ID NO: 11:

(i) SEQUENCE CHARACTERISTICS:
        (A) LENGTH: 15 amino acids
        (B) TYPE: amino acid
        (D) TOPOLOGY: linear (i i) MOLECULE TYPE: peptide (i i i) HYPOTHETICAL: No (v i) ORIGINAL SOURCE:
        (A) ORGANISM: Hepatitis C virus (v i i i) POSITION IN GENOME:
        (A) CHROMOSOME/SEGMENT: NS5

(x i) SEQUENCE DESCRIPTION: SEQ ID NO: 11:

```
Ser Arg Arg Phe Ala Gln Ala Leu Pro Val Trp Ala Arg Pro Asp
1               5                   10                  15
```

(2) INFORMATION FOR SEQ ID NO: 12:

(i) SEQUENCE CHARACTERISTICS:
        (A) LENGTH: 16 amino acids
        (B) TYPE: amino acid
        (D) TOPOLOGY: linear (i i) MOLECULE TYPE: peptide (i i i) HYPOTHETICAL: No (v i) ORIGINAL SOURCE:
        (A) ORGANISM: Hepatitis C virus (v i i i) POSITION IN GENOME:
        (A) CHROMOSOME/SEGMENT: Core (x i) SEQUENCE DESCRIPTION: SEQ ID NO: 12:

```
Pro Gln Asp Val Lys Phe Pro Gly Gly Gly Gln Ile Val Gly Gly Val
1               5                   10                  15
```

(2) INFORMATION FOR SEQ ID NO: 13:

(i) SEQUENCE CHARACTERISTICS:
        (A) LENGTH: 12 amino acids
        (B) TYPE: amino acid
        (D) TOPOLOGY: linear (i i) MOLECULE TYPE: peptide (i i i) HYPOTHETICAL: No (v i) ORIGINAL SOURCE:
        (A) ORGANISM: Hepatitis C virus (v i i i) POSITION IN GENOME:
        (A) CHROMOSOME/SEGMENT: NS4

( x i ) SEQUENCE DESCRIPTION: SEQ ID NO: 13:

Glu Glu Ala Ser Gln His Leu Pro Tyr Ile Glu Gln
1               5                       10

( 2 ) INFORMATION FOR SEQ ID NO: 14:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( i i i ) HYPOTHETICAL: No ( v i ) ORIGINAL SOURCE:
        ( A ) ORGANISM: Hepatitis C Virus ( v i i i ) POSITION IN GENOME:
        ( A ) CHROMOSOME/SEGMENT: NS4

( x i ) SEQUENCE DESCRIPTION: SEQ ID NO: 14:

Gln Lys Ala Leu Gly Leu Leu Gln Thr
1               5

( 2 ) INFORMATION FOR SEQ ID NO: 15:

( i ) SEQUENCE CHARACTERISTICS:
        ( A ) LENGTH: 18 amino acids
        ( B ) TYPE: amino acid
        ( D ) TOPOLOGY: linear ( i i ) MOLECULE TYPE: peptide ( i i i ) HYPOTHETICAL: No ( v i ) ORIGINAL SOURCE:
        ( A ) ORGANISM: Hepatitis C Virus ( v i i i ) POSITION IN GENOME:
        ( A ) CHROMOSOME/SEGMENT: NS4

( x i ) SEQUENCE DESCRIPTION: SEQ ID NO: 15:

Ser Arg Gly Asn His Val Ser Pro Thr His Tyr Val Pro Glu Ser Asp
1               5                       10                      15
Ala Ala ( 2 ) INFORMATION FOR SEQ ID NO: 16:

( i ) SEQUENCE CHARACTERISTICS:
        ( A ) LENGTH: 28 amino acids
        ( B ) TYPE: amino acid
        ( D ) TOPOLOGY: linear ( i i ) MOLECULE TYPE: peptide ( i i i ) HYPOTHETICAL: No ( v i ) ORIGINAL SOURCE:
        ( A ) ORGANISM: Hepatitis C Virus ( v i i i ) POSITION IN GENOME:
        ( A ) CHROMOSOME/SEGMENT: Core ( x i ) SEQUENCE DESCRIPTION: SEQ ID NO: 16:

Pro Gln Arg Lys Asn Lys Arg Asn Thr Asn Arg Arg Pro Gln Asp Val
1               5                       10                      15
Lys Phe Pro Gly Gly Gly Gln Ile Val Gly Val Val
                20                      25

( 2 ) INFORMATION FOR SEQ ID NO: 17:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: peptide ( i i i ) HYPOTHETICAL: No ( v i ) ORIGINAL SOURCE:
        ( A ) ORGANISM: Hepatitis C Virus ( v i i i ) POSITION IN GENOME:
        ( A ) CHROMOSOME/SEGMENT: NS3

( x i ) SEQUENCE DESCRIPTION: SEQ ID NO: 17:

```
Ala  Trp  Tyr  Glu  Leu  Thr  Pro  Ala  Glu  Thr  Thr  Val  Arg  Leu  Arg  Ala
1                  5                      10                         15
Tyr  Met  Asn  Thr  Pro  Gly  Leu  Pro  Val
                20                      25
```

( 2 ) INFORMATION FOR SEQ ID NO:18:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note=
            " digoxigenin-3-cme-beta-alanine-epsilon-aminocaproic
            acid-beta- alanine group is attached to the Asn at
            position 1."

( x i ) SEQUENCE DESCRIPTION: SEQ ID NO:18:

```
Asn  Asn  Thr  Arg  Lys  Ser  Ile  Ser  Ile  Gly  Pro  Gly  Arg  Ala  Phe  Tyr
1                  5                      10                         15
Thr
```

( 2 ) INFORMATION FOR SEQ ID NO:19:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Modified-site
        ( B ) LOCATION: 1
        ( D ) OTHER INFORMATION: /note=
            " digoxigenin-3-cme-beta-alanine-epsilon-aminocaproic
            acid is attached to the Asn at the 1 position."

( x i ) SEQUENCE DESCRIPTION: SEQ ID NO:19:

```
Asn  Thr  Thr  Arg  Ser  Ile  Ser  Ile  Gly  Pro  Gly  Arg  Ala  Phe  Tyr
1                  5                      10                         15
```

( 2 ) INFORMATION FOR SEQ ID NO:20:

( i ) SEQUENCE CHARACTERISTICS:
        ( A ) LENGTH: 19 amino acids
        ( B ) TYPE: amino acid ( C ) STRANDEDNESS: single
( D ) TOPOLOGY: linear ( i i ) MOLECULE TYPE: protein ( i x ) FEATURE:
    ( A ) NAME/KEY: Modified-site
    ( B ) LOCATION: 1
    ( D ) OTHER INFORMATION: /note=
        " digoxigenin-3-cme-beta-alanine-epsilon-aminocaproic
        acid-beta- alanine is attached to the Ile at the 1
        position."

( x i ) SEQUENCE DESCRIPTION: SEQ ID NO:20:

```
Ile Asp Ile Gln Glu Glu Arg Arg Met Arg Ile Gly Pro Gly Met Ala
1               5                   10                  15
Trp Tyr Ser
```

( 2 ) INFORMATION FOR SEQ ID NO:21:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: protein ( i x ) FEATURE:
    ( A ) NAME/KEY: Modified-site
    ( B ) LOCATION: 1
    ( D ) OTHER INFORMATION: /note=
        " digoxigenin-3-cme-beta-alanine-epsilon-aminocaproic
        acid-beta- alanine is attached to the Ala at the 1
        position."

( x i ) SEQUENCE DESCRIPTION: SEQ ID NO:21:

```
Ala Val Glu Arg Tyr Leu Lys Asp Gln Gln Leu Leu Gly Ile Trp
1               5                   10                  15
```

( 2 ) INFORMATION FOR SEQ ID NO:22:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: protein ( i x ) FEATURE:
    ( A ) NAME/KEY: Modified-site
    ( B ) LOCATION: 1
    ( D ) OTHER INFORMATION: /note=
        " digoxigenin-3-cme-epsilon-aminocaproic
        acid-beta- alanine-epsilon-aminocaproic acid-beta-alanine
        is attached to the Ala at the 1 position."

( x i ) SEQUENCE DESCRIPTION: SEQ ID NO:22:

```
Ala Val Glu Arg Tyr Leu Lys Asp Gln Gln Leu Leu Gly Ile Trp
1               5                   10                  15
```

( 2 ) INFORMATION FOR SEQ ID NO:23:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear ( i i ) MOLECULE TYPE: protein ( i x ) FEATURE:

(A) NAME/KEY: Modified-site
(B) LOCATION: 1
(D) OTHER INFORMATION: /note=
" digoxigenin-3-cme-beta-alanine-epsilon-aminocaproic acid
is attached to the Gln at the 1 position."

(xi) SEQUENCE DESCRIPTION: SEQ ID NO:23:

```
Gln Ala Arg Ile Leu Ala Val Glu Arg Tyr Leu Lys Asp Gln Gln Leu
1               5                   10                  15
Leu Gly Ile Trp Gly Ala Ser Gly
            20
```

(2) INFORMATION FOR SEQ ID NO:24:

(i) SEQUENCE CHARACTERISTICS:
        (A) LENGTH: 28 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Modified-site
        (B) LOCATION: 1
        (D) OTHER INFORMATION: /note=
" digoxigenin-3-cme-epsilon-aminocaproic acid is attached
to the Gly at the 1 position."

(xi) SEQUENCE DESCRIPTION: SEQ ID NO:24:

```
Gly Gly Gly Gly Gln Ala Arg Ile Leu Ala Val Glu Arg Tyr Leu Lys
1               5                   10                  15
Asp Gln Gln Leu Leu Gly Ile Trp Gly Ala Ser Gly
            20                  25
```

(2) INFORMATION FOR SEQ ID NO:25:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Modified-site
        (B) LOCATION: 1
        (D) OTHER INFORMATION: /note=
" digoxigenin-3-cme-beta-alanine-epsilon-aminocaproic
acid-beta- alanine is attached to the Trp at the 1
position."

(xi) SEQUENCE DESCRIPTION: SEQ ID NO:25:

```
Trp Gly Ile Arg Gln Leu Arg Ala Arg Leu Leu Ala Leu Glu Thr Leu
1               5                   10                  15
Leu Gln Asn
```

(2) INFORMATION FOR SEQ ID NO:26:

(i) SEQUENCE CHARACTERISTICS:
        (A) LENGTH: 32 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Modified-site
        (B) LOCATION: 1

( D ) OTHER INFORMATION: /note=
" digoxigenin-3-cme-beta-alanine-epsilon-aminocaproic
acid-beta- alanine is attached to the Leu at the 1
position."

( i x ) FEATURE:
( A ) NAME/KEY: Modified-site
( B ) LOCATION: 26
( D ) OTHER INFORMATION: /note= "cme-3-digoxigenin is
attached to the Leu at the 26 position."

( x i ) SEQUENCE DESCRIPTION: SEQ ID NO:26:

Leu Gly Ile Trp Gly Cys Ser Gly Lys Leu Ile Cys Thr Thr Ala Val
1               5                   10                  15
Leu Gly Ile Trp Gly Cys Ser Gly Lys Leu Ile Cys Thr Thr Ala Val
                20                  25                  30

( 2 ) INFORMATION FOR SEQ ID NO:27:

( i ) SEQUENCE CHARACTERISTICS:
( A ) LENGTH: 16 amino acids
( B ) TYPE: amino acid
( C ) STRANDEDNESS: single
( D ) TOPOLOGY: linear ( i i ) MOLECULE TYPE: protein ( i x ) FEATURE:
( A ) NAME/KEY: Modified-site
( B ) LOCATION: 1
( D ) OTHER INFORMATION: /note=
" digoxigenin-3-cme-beta-alanine-epsilon-aminocaproic
acid-beta- alanine is attached to the Leu at the 1
position."

( i x ) FEATURE:
( A ) NAME/KEY: Modified-site
( B ) LOCATION: 10
( D ) OTHER INFORMATION: /note= "cme-3-digoxigenin is
attached to the Leu at the 10 position."

( x i ) SEQUENCE DESCRIPTION: SEQ ID NO:27:

Leu Gly Ile Trp Gly Cys Ser Gly Lys Leu Ile Cys Thr Thr Ala Val
1               5                   10                  15

( 2 ) INFORMATION FOR SEQ ID NO:28:

( i ) SEQUENCE CHARACTERISTICS:
( A ) LENGTH: 59 amino acids
( B ) TYPE: amino acid
( C ) STRANDEDNESS: single
( D ) TOPOLOGY: linear ( i i ) MOLECULE TYPE: protein ( i x ) FEATURE:
( A ) NAME/KEY: Modified-site
( B ) LOCATION: 1
( D ) OTHER INFORMATION: /note=
" digoxigenin-3-cme-epsilon-aminocaproic
acid-beta- alanine is attached to the Gly at the 1
position."

( i x ) FEATURE:
( A ) NAME/KEY: Modified-site
( B ) LOCATION: 25
( D ) OTHER INFORMATION: /note= "cme-3-digoxigenin is
attached to the Leu at the 25 position."

( i x ) FEATURE:
( A ) NAME/KEY: Modified-site
( B ) LOCATION: 59
( D ) OTHER INFORMATION: /note= "cme-3-digoxigenin is
attached to the Gly at the 59 position."

( x i ) SEQUENCE DESCRIPTION: SEQ ID NO:28:

| Gly | Cys | Ser | Gly | Lys | Leu | Ile | Cys | Thr | Thr | Ala | Val | Pro | Trp | Asn | Ala |
|---|---|---|---|---|---|---|---|---|---|---|---|---|---|---|---|
| 1 | | | | 5 | | | | | 10 | | | | | 15 | |

| Ser | Trp | Ser | Gly | Cys | Ser | Gly | Lys | Leu | Ile | Cys | Thr | Thr | Ala | Val | Pro |
|---|---|---|---|---|---|---|---|---|---|---|---|---|---|---|---|
| | | | 20 | | | | | 25 | | | | | 30 | | |

| Trp | Asn | Ala | Ser | Trp | Ser | Gly | Cys | Ser | Gly | Lys | Leu | Ile | Cys | Thr | Thr |
|---|---|---|---|---|---|---|---|---|---|---|---|---|---|---|---|
| | | 35 | | | | | 40 | | | | | 45 | | | |

| Ala | Val | Pro | Trp | Asn | Ala | Ser | Trp | Ser | Lys | Gly |
|---|---|---|---|---|---|---|---|---|---|---|
| 50 | | | | | | 55 | | | | |

( 2 ) INFORMATION FOR SEQ ID NO:29:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Modified-site
        ( B ) LOCATION: 1
        ( D ) OTHER INFORMATION: /note=
            " digoxigenin-3-cme-beta-alanine-epsilon-aminocaproic acid-beta- alanine is attached to the Leu at the 1 position."

( x i ) SEQUENCE DESCRIPTION: SEQ ID NO:29:

| Leu | Ser | Leu | Trp | Gly | Cys | Lys | Gly | Lys | Leu | Val | Cys | Tyr | Thr | Ser |
|---|---|---|---|---|---|---|---|---|---|---|---|---|---|---|
| 1 | | | | 5 | | | | | 10 | | | | | 15 |

( 2 ) INFORMATION FOR SEQ ID NO:30:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Modified-site
        ( B ) LOCATION: 1
        ( D ) OTHER INFORMATION: /note=
            " digoxigenin-3-cme-beta-alanine-epsilon-aminocaproic acid-beta- alanine is attached to the Lys at the 1 position."

( x i ) SEQUENCE DESCRIPTION: SEQ ID NO:30:

| Lys | Asp | Gln | Gln | Leu | Leu | Gly | Ile | Trp | Gly | Ser | Ser | Gly | Lys | Leu |
|---|---|---|---|---|---|---|---|---|---|---|---|---|---|---|
| 1 | | | | 5 | | | | | 10 | | | | | 15 |

( 2 ) INFORMATION FOR SEQ ID NO:31:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Modified-site
        ( B ) LOCATION: 1
        ( D ) OTHER INFORMATION: /note=
            " digoxigenin-3-cme-beta-alanine-epsilon-aminocaproic acid-beta- alanine is attached to the Ala at the 1 position."

(x i) SEQUENCE DESCRIPTION: SEQ ID NO:31:

Ala Leu Glu Thr Leu Leu Gln Asn Gln Leu Leu Ser Leu Trp
1               5                   10

(2) INFORMATION FOR SEQ ID NO:32:

(i) SEQUENCE CHARACTERISTICS:
        (A) LENGTH: 14 amino acids
        (B) TYPE: amino acid
        (C) STRANDEDNESS: single
        (D) TOPOLOGY: linear (i i) MOLECULE TYPE: protein (i x) FEATURE:
        (A) NAME/KEY: Modified-site
        (B) LOCATION: 1
        (D) OTHER INFORMATION: /note=
            " digoxigenin-3-cme-epsilon-aminocaproic acid is attached
            to the Asn at the 1 position."

(x i) SEQUENCE DESCRIPTION: SEQ ID NO:32:

Asn Ser Trp Gly Cys Ala Phe Arg Gln Val Cys His Thr Thr
1               5                   10

(2) INFORMATION FOR SEQ ID NO:33:

(i) SEQUENCE CHARACTERISTICS:
        (A) LENGTH: 15 amino acids
        (B) TYPE: amino acid
        (C) STRANDEDNESS: single
        (D) TOPOLOGY: linear (i i) MOLECULE TYPE: protein (i x) FEATURE:
        (A) NAME/KEY: Modified-site
        (B) LOCATION: 1
        (D) OTHER INFORMATION: /note=
            " digoxigenin-3-cme-beta-alanine-epsilon-aminocaproic
            acid-beta- alanine is atttached to the Ser at the 1
            position."

(x i) SEQUENCE DESCRIPTION: SEQ ID NO:33:

Ser Arg Arg Phe Ala Gln Ala Leu Pro Val Trp Ala Arg Pro Asp
1               5                   10                  15

(2) INFORMATION FOR SEQ ID NO:34:

(i) SEQUENCE CHARACTERISTICS:
        (A) LENGTH: 16 amino acids
        (B) TYPE: amino acid
        (C) STRANDEDNESS: single
        (D) TOPOLOGY: linear (i i) MOLECULE TYPE: protein (i x) FEATURE:
        (A) NAME/KEY: Modified-site
        (B) LOCATION: 1
        (D) OTHER INFORMATION: /note=
            " digoxigenin-3-cme-beta-alanine is attached to the Pro
            at the 1 position."

(x i) SEQUENCE DESCRIPTION: SEQ ID NO:34:

Pro Gln Asp Val Lys Phe Pro Gly Gly Gly Gln Ile Val Gly Gly Val
1               5                   10                  15

(2) INFORMATION FOR SEQ ID NO:35:

(i) SEQUENCE CHARACTERISTICS:

( A ) LENGTH: 12 amino acids
( B ) TYPE: amino acid
( C ) STRANDEDNESS: single
( D ) TOPOLOGY: linear ( i i ) MOLECULE TYPE: protein ( i x ) FEATURE:
( A ) NAME/KEY: Modified-site
( B ) LOCATION: 1
( D ) OTHER INFORMATION: /note=
" digoxigenin-3-cme-beta-alanine-beta-ananine-norleucine
is attached to the Glu at the 1 position."

( x i ) SEQUENCE DESCRIPTION: SEQ ID NO:35:

| Glu | Glu | Ala | Ser | Gln | His | Leu | Pro | Tyr | Ile | Glu | Gln |
| 1 | | | | 5 | | | | | 10 | | |

( 2 ) INFORMATION FOR SEQ ID NO:36:

( i ) SEQUENCE CHARACTERISTICS:
( A ) LENGTH: 9 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Modified-site
( B ) LOCATION: 1
( D ) OTHER INFORMATION: /note=
" digoxigenin-3-cme-beta-alanine-beta-alanine is attached
to the Gln at the 1 position."

( x i ) SEQUENCE DESCRIPTION: SEQ ID NO:36:

Gln Lys Ala Leu Gly Leu Leu Gln Thr
1               5

( 2 ) INFORMATION FOR SEQ ID NO:37:

( i ) SEQUENCE CHARACTERISTICS:
( A ) LENGTH: 18 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Modified-site
( B ) LOCATION: 1
( D ) OTHER INFORMATION: /note=
" digoxigenin-3-cme-beta-alanine-epsilon-aminocaproic
acid-beta- alanine is attached to the Ser at the 1
position."

( x i ) SEQUENCE DESCRIPTION: SEQ ID NO:37:

Ser Arg Gly Asn His Val Ser Pro Thr His Tyr Val Pro Glu Ser Asp
1               5                   10                  15
Ala Ala ( 2 ) INFORMATION FOR SEQ ID NO:38:

( i ) SEQUENCE CHARACTERISTICS:
( A ) LENGTH: 9 amino acids
( B ) TYPE: amino acid
( C ) STRANDEDNESS: single
( D ) TOPOLOGY: linear ( i i ) MOLECULE TYPE: peptide ( i x ) FEATURE:

(A) NAME/KEY: Modified-site
(B) LOCATION: 1
(D) OTHER INFORMATION: /note=
 " digoxigenin-3-cme-beta-alanine-epsilon-aminocaproic
 acid-beta- alanine is attached to the Lys at the 1
 position."

(xi) SEQUENCE DESCRIPTION: SEQ ID NO:38:

```
Lys Asn Lys Arg Asn Thr Asn Arg Arg
1               5
```

(2) INFORMATION FOR SEQ ID NO:39:

(i) SEQUENCE CHARACTERISTICS:
 (A) LENGTH: 28 amino acids
 (B) TYPE: amino acid
 (C) STRANDEDNESS: single
 (D) TOPOLOGY: linear (ii) MOLECULE TYPE: peptide (ix) FEATURE:
 (A) NAME/KEY: Modified-site
 (B) LOCATION: 1
 (D) OTHER INFORMATION: /note=
  " digoxigenin-3-cme-beta-alanine is attached to the Pro
  at the 1 position."

(xi) SEQUENCE DESCRIPTION: SEQ ID NO:39:

```
Pro Gln Arg Lys Asn Lys Arg Asn Thr Asn Arg Arg Pro Gln Asp Val
1               5                   10                  15
Lys Phe Pro Gly Gly Gly Gln Ile Val Gly Val Val
            20                  25
```

(2) INFORMATION FOR SEQ ID NO:40:

(i) SEQUENCE CHARACTERISTICS:
 (A) LENGTH: 25 amino acids
 (B) TYPE: amino acid
 (C) STRANDEDNESS: single
 (D) TOPOLOGY: linear (ii) MOLECULE TYPE: peptide (ix) FEATURE:
 (A) NAME/KEY: Modified-site
 (B) LOCATION: 1
 (D) OTHER INFORMATION: /note=
  " digoxigenin-3-cme-beta-alanine-epsilon-aminocaproic acid
  is attached to the Ala at the 1 position."

(xi) SEQUENCE DESCRIPTION: SEQ ID NO:40:

```
Ala Trp Tyr Glu Leu Thr Pro Ala Glu Thr Thr Val Arg Leu Arg Ala
1               5                   10                  15
Tyr Met Asn Thr Pro Gly Leu Pro Val
            20                  25
```